United States Patent [19]

Klemann et al.

[11] Patent Number: 5,380,544
[45] Date of Patent: Jan. 10, 1995

[54] PRODUCTION OF FAT MIXTURES ENRICHED WITH TRIGLYCERIDES BEARING SHORT, MEDIUM AND LONG RESIDUES

[75] Inventors: Lawrence P. Klemann, Somerville, N.J.; Allan D. Roden, Noblesville, Ind.; Turiddu A. Pelloso, Carmel, Ind.; Gilbert L. Boldt, Indianapolis, Ind.

[73] Assignee: Nabisco, Inc., Parsippany, N.J.

[21] Appl. No.: 26,894

[22] Filed: Mar. 5, 1993

Related U.S. Application Data

[63] Continuation-in-part of Ser. No. 804,140, Dec. 6, 1991, Pat. No. 5,258,197, which is a continuation-in-part of Ser. No. 624,056, Dec. 7, 1990, abandoned, which is a continuation-in-part of Ser. No. 410,161, Sep. 20, 1989, abandoned.

[51] Int. Cl.$^6$ ............................................. A23D 9/00
[52] U.S. Cl. ..................................... 426/607; 426/610; 426/660
[58] Field of Search ............... 426/607, 613, 804, 601, 426/610, 660

[56] References Cited

U.S. PATENT DOCUMENTS

| | | | |
|---|---|---|---|
| 5,023,106 | 6/1991 | Ehrman | 426/607 |
| 5,188,858 | 2/1993 | Stipp | 426/804 |
| 5,258,197 | 11/1993 | Wheeler | 426/607 |

FOREIGN PATENT DOCUMENTS 2-158695  6/1990  Japan.

OTHER PUBLICATIONS

CA 118(5)37817c.
CA 73(15)73333c.
Norden et al. 1980 Anthophora bees: unusual glycerides from maternal Dufour's glands serve as larval food and cell lining.
CA 93(5)41922r.
Ambrose, A. M. and Robbins, D. J., J. Nutr. 58: 113–124 (1956).
Babayan, V. K., Beare-Rogers, J., ed., Dietary Fat Requirements in Health and Development, A.O.C.S. 1988.
Baur, F. J., J. Amer. Oil Chem. Soc. 31: 147–151 and 196–199 (1954).
Beare-Rogers, J., ed., Dietary Fat Requirements in Health and Development, A.O.C.S. (1988).
Bonanome, A. and Grundy, S. M., New Eng. Jour. Med. 318: 1244–1248 (1988).
Coleman, R. D., et al., J. Amer. Oil Chem. Soc. 40: 737–742 (1963).
Feuge, R. O., Food Technology 9: 314–318 (1955).
Kaunitz, H., et al., J. Amer. Oil Chem. Soc. 35: 10–13 (1957).
Mattson, F. H., et al., J. Nutr. 59: 277–285 (1956).
Mensink, R. P. and Katan, M. B., New Eng. Jour. Med., 323: 439–445 (1990).

*Primary Examiner*—Carolyn Paden

[57] ABSTRACT

Fat mixtures containing at least about 24%, more preferably at least about 34%, triglycerides bearing short, medium, and long residues are prepared. Many embodiments contain at least about 50%, and some at least about 75% to 90%, of these triglycerides, and have an acyl carbon number of 26 to 36. Especially preferred short substituents are derived from acetic acid, butyric acid, and mixtures of these with each other and with propionic acid. Especially preferred medium substituents have at least about 90% of the residues derived from capric acid, caprylic acid, and mixtures of these. Especially preferred long substituents contain at least about 70%, and many have at least about 85%, stearic acid or behenic acid residues or mixtures of these. One embodiment has an acyl carbon number of 28 to 32 and the long residues are predominantly stearic acid residues. Another embodiment has an acyl carbon number of 32 to 36 and the long residues are predominantly behenic acid residues. These fats may be prepared by interesterifying a mixture of triglycerides bearing short residues and triglycerides bearing medium residues with triglycerides bearing long residues and steam deodorizing the product at relatively high temperatures. The steam deodorized product can be further enriched with triglyceride species bearing short, medium, and long residues using molecular distillation.

14 Claims, No Drawings

5,380,544

PRODUCTION OF FAT MIXTURES ENRICHED WITH TRIGLYCERIDES BEARING SHORT, MEDIUM AND LONG RESIDUES

RELATED U.S. APPLICATION DATA

This is a continuation-in-part of co-pending U.S. application Ser. No. 804,140, now U.S. Pat. No. 5,258,147 filed Dec. 6, 1991, hereby incorporated in its entirety by reference, which was a continuation-in-part of U.S. application Ser. No. 07/624,056, filed Dec. 7, 1990, now abandoned, which was a continuation-in-part of U.S. application Ser. No. 07/410,161, filed on Sep. 20, 1989, now abandoned.

TECHNICAL FIELD

This invention relates to the production of fat compositions containing triglycerides bearing short, medium, and long residues.

Dietary fat is the most concentrated source of energy of all the nutrients, supplying about double that contributed by either carbohydrate or protein. Though high in calories, fat contributes to the palatability and flavor of food, since most food flavors are fat-soluble, and to the satiety value, since fatty foods remain in the stomach for longer periods of time than do foods containing protein and carbohydrate. Furthermore, fat is a carrier of the fat-soluble vitamins, A, D, E, and K, and the essential fatty acids, which have been shown to be important in growth and in the maintenance of many body functions. Hence, major research efforts have focused on ways to produce low calorie fats and fat mimetics that provide the same functional and organoleptic properties as fats, but not the calories.

Some low calorie fats have been prepared using fatty acids of diminished caloric value, but because the array of these acids is small, fats prepared using them exhibit limited functionality. Synthetic fat mimetics have been created and are now undergoing testing for safety. Unfortunately, many consumers are concerned with the synthetic connotation of food additives of this type and will not avail themselves of the advantages they offer.

There is a need for fats that are low in calories, yet which have desirable functional properties and are not perceived as artificial.

BACKGROUND ART

Neutral fats, the most abundant group of lipids in nature, are fatty acid triesters of glycerol. Fatty acids are divided by their occurrence and/or properties into three major groups: short, also called volatile $C_2$ to $C_4$ fatty acids, medium, also called kernel or lauric fat $C_6$ to $C_{12}$ fatty acids, and long $C_{14}$ to $C_{24}$ fatty acids. Most natural fats contain an array of the last group of fatty acids.

Fats have been produced by substituting acetic acid for a portion of the fatty acids occurring in ordinary fats or oils, thus comprising triglycerides bearing short acetyl and long substituents. These acetoglycerides were investigated during the 1950's and found to be digestible. Feeding studies indicated that the nutritive value of mono- and diacetin fats were essentially the same as those of animals fed the corresponding conventional triglycerides (Mattson, F. H., et al., *J. Nutr.* 59: 277–285 (1956), although acetooleins were more digestible than acetostearins (Ambrose, A. M., and Robbins, D. J., *J. Nutr.* 58: 113–124 (1956) and animals grew poorly when fed acetostearin as the sole dietary fat (Coleman, R. D., et al., *J. Amer. Oil Chem. Soc.* 40: 737–742 (1963)).

Acetostearins are waxy fats having sharp melting points, which has limited their application to food products requiring plastic or liquid fats. In contrast to fats bearing medium and/or long substituents, acetostearins also exhibit unusual polymorphism (Baur, F. J., *J. Amer. Oil Chem. Soc.* 31: 147–151 and 196–199 (1954) and Feuge, R. O., *Food Technology* 9: 314–318 (1955)). Because of their melting and crystal properties, the fats have been suggested as useful for plasticizers, thin films, and coatings for such food products as meat, fish, and cheese (U.S. Pat. No. 2,615,159 to Jackson and U.S. Pat. No. 2,615,160 to Baur). Compositions of this nature have been referred to as "hot melts" and may contain antibiotics (U.S. Pat. No. 3,192,057 to Hines and Shirk) or polymeric materials (U.S. Pat. No. 3,388,085 to Levkoff and Phillips) to prolong the life of the coating.

In contrast to triglycerides bearing long chain fatty acids, medium chain triglycerides, generally obtained from kernel oils or lauric fats and encompassing those substituted with $C_6$ to $C_{12}$, predominantly $C_8$ to $C_{10}$, fatty acids are more rapidly absorbed and metabolized via a different catabolic route (see a recent review by Babayan, V. K., in Beare-Rogers, J., ed., *Dietary Fat Requirements in Health and Development*, A.O.C.S. 1988, chapter 5, pages 73 to 86). Hence, medium chain triglycerides have been employed in premature infant formulas and in the treatment of several malabsorption syndromes (ibid.). Feeding studies by H. Kaunitz, et al., demonstrated the usefulness of medium chain triglycerides in weight maintentance and obesity control in rats (*J. Amer. Oil Chem. Soc.* 35:10–13 (1957)).

Several research groups have exploited the physical and nutritional properties of medium chain fatty acids by suggesting that triglycerides having stearic and/or behenic acid in combination with medium chain substituents be used as low calorie fats (U.S. Pat. No. 5,066,510 to Ehrman, et al. and Jap. Pat. Pub. No. 2-158,695 to Yoshida, et al.). Because of their melting profiles, these fats have been suggested primarily for use as cocoa butter substitutes.

The polymorphism of triglycerides bearing medium and long moieties generally resembles fats bearing long moieties in that they tend to have a stable beta crystal structure. This contributes to graininess of fat mixtures containing them. The preparation of smooth blends requires careful substituent selection or tempering. It would be desirable to have low calorie fat mixtures free of this disadvantage.

It would also be desirable to formulate low calorie fats having enhanced structural and functional diversity that exhibit properties appropriate for various kinds of food products.

DISCLOSURE OF THE INVENTION

A principal object of the present invention is to provide a new group of low calorie triglycerides having a broad distribution of molecular weight species resulting in functional characteristics for a variety of food products.

It is a further and more specific object of the invention to provide for the production of fat mixtures enriched with low calorie fats that exhibit unique melting characteristics.

These and other objects are accomplished by the present invention, which provides mixtures containing at least about 50% and, in some embodiments at least about 80%, triglycerides which have an acyl carbon number of 26 to 36 and which bear short $C_2$ to $C_4$ acid residues, medium $C_6$ to $C_{12}$ fatty acid residues, and long, saturated $C_{16}$ to $C_{22}$ fatty acid residues. Denoting the aliphatic portion of the long fatty acid substituent as L, the medium as M, and the short as S, the fat mixtures of this invention contain SML, SLM, and MSL species.

Especially preferred short substituents are derived from acetic acid, propionic acid, butyric acid, and mixtures of these. Especially preferred medium substituents have at least about 90% of the residues derived from capric acid, caprylic acid and mixtures of these. In one embodiment, the triglyceride mixtures have an acyl carbon number of 28 to 32 and the long residues are predominantly stearic acid residues. In another embodiment, the triglyceride mixtures have an acyl carbon number of 32 to 36 and the long residues are predominantly behenic acid residues.

The fat mixtures of this invention having a carbon number of 26 to 36 may be prepared by interesterifying a mixture of triglycerides bearing short residues and triglycerides bearing medium residues with triglycerides bearing long residues and then steam deodorizing the product at relatively high temperatures, e.g., from about 210° to about 260° C. The steam deodorized product can be further enriched with SML, SLM and MSL species by molecular distillation.

Triglyceride blends of this invention exhibit surprising properties. Some embodiments are liquid, though the fats are fully saturated. Others are plastic over wide temperature ranges and spreadable at refrigerator temperatures, having stable, non-grainy crystal structures.

GENERAL DESCRIPTION OF THE INVENTION

This invention is based upon the finding that the physical properties of low calorie fats, notably their melting profiles and crystal structures, can be drastically changed by the incorporation of triglycerides bearing short, medium, and long moieties.

Denoting the aliphatic portion of short moieties as S, the medium as M, and the long as L, preferred fats of this invention contain at least about 24%, preferably at least about 34%, and in some embodiments at least about 50% to 80%, or higher, triglycerides selected from the group consisting of

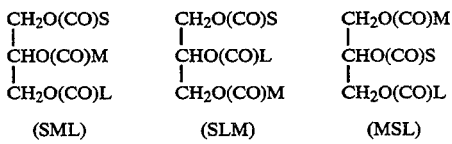

(SML)    (SLM)    (MSL)

and mixtures of these,
where
each L group is, independently, a long chain saturated aliphatic group having 15 to 21 carbons;
each M group is, independently, a medium chain saturated aliphatic group having 5 to 11 carbons; and
each S, independently, is a short chain group having 1 to 3 carbons.
Many embodiments contain a mixture of at least about 75%, and some at least about 90%, of these SML/SLM/MSL triglycerides.

In preferred triglycerides, the short moieties are derived from acetic acid, propionic acid, butyric acid, or a mixture of these. Especially preferred short moieties comprise a mixture of acetic and propionic acid, butyric acid, a mixture of acetic and butyric acid, or a mixture of these. These especially preferred embodiments have at least about 90% of their medium moieties derived from caprylic acid, capric acid, or a mixture of these acids. And the long moieties of these embodiments have at least about 70%, and in many cases at least about 85%, derived from stearic acid or behenic acid or a mixture of these acids.

One especially preferred embodiment comprises triglyceride mixtures having an acyl carbon number (ACN) of 28 to 32 and the long residues are predominantly stearic acid residues. In another embodiment, the triglyceride mixtures have an acyl carbon number of 32 to 36 and the long residues are predominantly behenic acid residues.

Depending upon the preparative procedure (more fully discussed below), triglyceride mixtures of this invention may also contain SSL, SLS, LLS, LSL, MML, MLM, MML, LLM, SSM, SMS, MMM, SSS, and LLL species, but preferred embodiments maximize the SML/SLM/MSL component using special synthetic techniques that manipulate the reactant ratios and reaction conditions. Purification techniques that strip off SSS, MMM, SSM, SMS, MMS, MSM, SSL, SLS, MML, MLM, and LLL species may also be employed. It is desirable to remove low molecular weight triglycerides that contribute off flavors.

In the practice of this invention, medium chain residues are incorporated into triglycerides bearing short and long residues in amounts sufficient to achieve a less sharp melting profile and a wider plastic range than that found in corresponding triglycerides bearing only short and long residues. For example, the substitution of as little as 3% of the short fatty acids in triglycerides bearing short and long residues with medium residues can provide a highly functional product, though higher degrees of substitution, e.g., up to 80%, are useful for some applications.

Preferred S groups are derived from acetic or butyric acid or mixtures of these with propionic acid and with each other. Preferred M groups are derived from predominantly, i.e., at least about 90%, a mixture of caprylic and capric acid. Preferred L groups are derived predominantly, i.e., at least about 70%, preferably at least about 75%, and in some embodiments at least about 90%, stearic acid or behenic acid or a mixture of these acids.

Short (volatile) acid residues have no more than 4 carbons. Short residues are derived from carboxylic acids of the formula SCOOH, where S is a short chain aliphatic group having 1 to 3 carbons. As denoted herein, where triglycerides are described as bearing pendant groups derived from acids having 2, 3, or 4 carbons, compositions derived from acids having predominantly 2, 3, or 4 carbons are included. Acylation of a glycerol hydroxyl by acid SCOOH results in the attachment of short chain S to the glycerol backbone by means of an ester linkage (—O—(CO)—). Where there is more than one short group attached to a glyceride, the groups may be the same or different. As used herein, the term "acid residue" refers to an acyl group comprising a short chain portion, here S, and a carbonyl group.

Short chain S may be straight or branched. Short chain S may be derived from any synthetic or natural organic acid including, but not limited to acetic (ethanoic), propionic (propanoic), butyric (butanoic), and the like acids. As used herein, chemical names include isomeric variations; for example, "butyric acid" includes normal-butyric acid (butanoic) and iso-butyric (2-methylpropanoic) acid, and so forth. Preferred acids are acetic, butyric, mixtures of acetic and butyric, mixtures of acetic and propionic, and mixtures of acetic, propionic, and butyric.

Medium chain M aliphatic groups are derived from any synthetic or natural organic medium chain fatty acid of the formula MCOOH, including, but not limited to caproic (hexanoic), caprylic (octanoic), pelargonic (nonanoic), captic (decanoic), lauric (dodecanoic) and the like acids. Preferred medium chain fatty acids contain predominantly, i.e., at least about 75%, preferably at least about 90% caprylic acid or capric acid, or mixtures of these acids.

The long saturated pendant groups are derived from fatty acids of the formula LCOOH, where L is a saturated aliphatic group having 15 to 39, preferably 15 to 21, carbons. L groups may be derived from any synthetic or natural, straight or branched saturated organic acid including, but not limited to, palmitic (hexadecanoic), stearic (octadecanoic), arachidic (eicosanoic), behenic (docosanoic), and the like acids.

Unsaturated long groups may also be present in the mixtures. These are derived from unsaturated acids of the formula UCOOH, where U is a $C_{15}$ to $C_{19}$ unsaturated group, including, but not limited to, palmitoleic (9-hexadecenoic), oleic (cis-9-octadecenoic), elaidic (trans-9-octadecenoic), vaccenic (trans-11-octadecenoic), linoleic (cis, cis-9,12-octadecedienoic), linolenic (9,12,15-octadecatrinoic and 6,9,12-octadecatrienoic), eleostearic (9,11,13-octadecatrienoic), arachidonic (5,8,11,14-eicosatetraenoic), and the like acids. L groups may be derived from U groups hydrogenated before or after incorporation into triglycerides.

S, M, and L groups may be derived from mixtures of acids, such as, for example, those derived from specific fractions of unhydrogenated, partially hydrogenated or fully hydrogenated dairy butterfat, coconut, palm kernel and the like oils and fats. For example, butterfat has been fractionated, yielding a fraction enriched with triglycerides having 2 residues of at least 16 carbons and 1 residue with 2 to 8 carbons (U.S. Pat. No. 4,479,976 to Lansbergen and Kemps, and U.S. Pat. No. 4,504,503 to Biernoth and Merk). Various L groups can be derived from mixtures of fatty acids obtained from natural oils such as soybean, safflower, sunflower, sesame, peanut, corn, olive, rice bran, mustard seed, cottonseed, poppyseed, rapeseed, marine, meadowfoam and the like oils; fats such as babassu nut oil, palm oil, tallow, lard, and shea butter; or plant waxes such as jojoba. Fat mixtures and/or fractions, crystallized fats, interesterified fats and mixtures of these may also be employed.

Mixtures of L groups are preferably derived from oils and fats that are hydrogenated, most preferably fully hydrogenated. Fully hydrogenated fats typically have an Iodine Value of 5 or less, and, in some cases, less than 2. Hydrogenated fats having at least about 70%, preferably at least about 75%, stearic acid residues such as, for example, hydrogenated peanut oil, hydrogenated olive oil, hydrogenated soybean oil, hydrogenated sesame oil, and hydrogenated corn oil are especially desirable. Some embodiments employ L moieties derived from hydrogenated fats having at least about 90% stearic acid residues, such as hydrogenated sunflower oil, hydrogenated safflower oil and hydrogenated canola. Embodiments having L moieties exhibiting a high in behenic acid content are derived from hydrogenated rapeseed, hydrogenated fish oil, and hydrogenated meadowfoam.

Other embodiments employ L moieties derived from a mixture of hydrogenated oils having pendant groups exhibiting greater chain length variety, such as, for example, L groups derived from a mixture of hydrogenated canola or soybean oil and rapeseed oil, hydrogenated canola or soybean oil and cottonseed oil, and the like. Because there is evidence that palmitic acid (like lauric and myristic acids) may increase plasma cholesterol concentrations (Bonanome, A., and Grundy, S. M., *New Eng. Jour. Med.* 318: 1244–1248 (1988)), preferred hydrogenated feedstocks are low in palmitic acid content. It is an advantage of the invention, however, that even those that are not low in palmitic yield low calorie fats having decreased palmitic acid since the short and medium residues replace a significant portion of the acid in the feedstock.

Some triglyceride mixtures of this invention contain about 15 to about 55 mole % short moieties, about 15 to about 60 mole % medium moieties, and about 20 to about 40 mole % long moieties. The molar ratio of short to the sum of medium and long residues of some preferred embodiments ranges between about 0.2 to 1.2. An example embodiment illustrated in the next section is a liquid oil fat mixture of triglycerides bearing about 14 mole % acetic acid, about 20 mole % propionic acid, about 27 mole % medium chain residues, and about 39 mole % long residues.

Many embodiments of this invention have short and medium to long molar ratios of about 5:1 to 20:1, more narrowly 10:1 to 15:1. An especially preferred embodiment has a short and medium to long molar ratio of 12:1. In preferred embodiments, at least 24%, preferably at least about 34%, of the triglycerides each bear one short, one medium, and one long moiety per molecule, i.e., are SML, SLM, or MSL triglycerides or a mixture of these species. Other embodiments have at least about 50% or at least about 80% of these species.

Short, medium, and long moieties are selected for the physical properties desired in the final product. Many embodiments have a short to medium molar ratio of about 1:1 to 10:1, more narrowly 2:1 to 8:1. An especially preferred embodiment has a short to long molar ratio of 8:3.5, or about 3:1.

MODES FOR CARRYING OUT THE INVENTION

Component triglycerides making up the low calorie fat mixtures of this invention are prepared using synthetic procedures known to those skilled in the art, such as, for example, directly esterifying glycerol or glycerol esters with fatty acids, fatty acid halides (notably chlorides) or fatty acid anhydrides, transesterifying glycerol with fatty acid esters, or interesterifying short, medium, and long triglycerides for such time and under such conditions that triglycerides bearing short, medium, and /Long residues form. Starting materials for triglyceride preparations may be obtained commercially or isolated from natural sources. Alternatively, component triglycerides may be isolated iron natural or processed fats or oils, or fractions thereof, as discussed above. Mixtures are purified using steam deodorization, filtration, fractional distillation and the like purification methods.

Desirable triglyceride mixtures enriched with SML, SLM, and MSL species are prepared using a random interesterification of short chain triglycerides (or triglycerides enriched with short chain moieties) and medium chain triglycerides (or triglycerides enriched with medium chain moieties) with long chain triglycerides, preferably triglycerides enriched with hydrogenated long chain residues, using reactant molar ratios that maximize the production of triglycerides bearing short, medium, and long moieties. A typical interesterification reaction contains about 6 to 9 moles short triglycerides, about 2.5 to 5 moles medium triglycerides and 1 mole fully hydrogenated oil, one embodiment contains 8.4 to 8.7 moles short triglycerides, 3 to 3.1 mole medium triglycerides, and 1.2 to 1.6 moles long triglycerides.

Purification ordinarily follows. Preferred methods are selected to maximize the isolation of SML/SLM/MSL species, for example, steam deodorization at relatively high temperatures, e.g., from about 210° to 260° C., that strip off SSS, SSM, SMS, MMS, MSM, MMM, SSL, and SLS species formed in the reaction. Mixtures even more enriched with SML/SLM/MSL species can be obtained by molecular distillation of the steam deodorized product. Using thence techniques, mixtures containing from about 75% to over 90% SML/SLM/MSL species can be obtained.

As can be seen from the data in the Examples that follow, adding medium chain triglycerides to an interesterification mixture of short and long triglycerides can drastically alter the melting profiles of the fat produced in the reaction. Substitution of half the short acids in a short/long mixture can convert, for example, a high and sharply melting coating fat to an oil liquid at 50° to 100° F. The proportions of reactants in preferred embodiments are selected to maximize the SML/SLM/MSL species in the product.

Preferred amounts of medium moieties flatten the melting curve and increase the plastic range of the corresponding fat having only short and long residues, or yield an entirely liquid oil. The nature and amount of medium residues are selected so that the overall mixture is more liquid or can remain semisolid over a wirer temperature range, having solids at 50° F. to 100° F. lower than the corresponding short/long fat.

To achieve desirable fat solids contents for certain food products, some low calorie triglycerides prepared using interesterification contain unsaturated residues. These are obtained by adding some liquid oil to the interesterification mixture containing short triglycerides, medium triglycerides, and long, saturated triglycerides (e.g., hydrogenated oils). Trans fatty acids have been recently shown to raise low density lipoprotein serum cholesterol levels and to lower high density lipoprotein serum cholesterol levels in adults fed fats having these acids (Mensink, R. P., and Katan, M. B., *New Eng. Jour. Med.,* 323: 439–445 (1990)), so, to keep the trans unsaturated levels to a minimum, unhydrogenated, natural oils are preferred. Where liquid oils are employed, the long, saturated triglycerides typically predominate, although a 1:1 molar ratio is desired in some embodiments. In these embodiments, typical molar ratios of liquid to hydrogenated oils range from about 0.1:1 to about 1:1, preferably about 0.5 to 1.

The triglycerides of this invention are low in calories. By this is meant they deliver fewer calories than a fat of the same type which does not bear short and medium chains, for example, delivering fewer than 8 kcal/gram upon being metabolized. Preferred low calorie triglycerides of this invention deliver about 6 kcal/gram or fewer calories upon being metabolized.

An advantage of the invention is that, because of the unique properties of triglyceride mixtures enriched with SML/SLM/MSL species, they can be used neat or mixed with hardstocks or soft stocks to obtain low calorie, low trans blends having suitable properties for a variety of food products.

The low calorie triglycerides are incorporated either alone, or in combination with one or more other fats or fat mimetics, into any food composition in amounts effective to provide sufficient plasticity to the fat component and/or in amounts effective to provide a significant caloric reduction of the calories due to fat. For example, a 10% or greater replacement would be effective for this purpose, and replacements of at least 25%, preferably at least 30%, more particularly 50 to 100%, are desired in many cases.

Exemplary food products which can be improved by replacing at least a portion of the usual fat component with the low calorie triglycerides of this invention are: baked foods, such as cookies, crackers, biscuits, cakes and the like which all contain at least a flour or starch component in addition to the low calorie triglycerides of this invention; snack products which are fried or coated with fat or oil and/or also contain at least a flour or starch component in addition to the low calorie triglycerides; emulsion products, such as margarine products (e.g., full-fat, low-fat, and fat substitute products), salad dressing and mayonnaise which all contain emulsions having a fat phase including the low calorie triglycerides and an aqueous phase; candies and confections which contain a sweetener such as sugar or aspartame in addition to the low-calorie triglycerides and a flavor such as chocolate; and dairy product substitutes which contain a dairy protein such as whey, casein or caseinate, or the like in addition to the low calorie triglycerides. The margarine products also typically contain a milk component and butter flavor, while the salad dressings will contain spices and the mayonnaise, egg. Among the baked products, cakes and cookies also contain sweeteners and the crackers typically contain salt.

The low calorie triglycerides of this invention are especially advantageous in shortening and margarine fat compositions and in food products having a liquid oil component such as salad dressings. One important function of a shortening is to hold air, whether beaten in a cake batter or creamed with other icing ingredients. This ability to hold air generally is increased by a plastic consistency of the shortening. Further, following baking, plastic shortenings remain dispersed within baked goods, whereas liquid shortenings have a tendency to leak and collect in pockets.

Fat mixtures are prepared to yield desirable solid fat index (S.F.I.) values for these products. S.F.I. is a measure of the solidity of fats at various temperatures; it is related to the percentage of a fat that exists in crystalline form at a given temperature. Typical shortening fat compositions of the invention have the following solid fat index:

| Temperatures | Solids (%) |
| --- | --- |
| 50° F. | at least 25 |
| 70° F. | at least 20 |
| 80° F. | 10 to 50 |
| 92° F. | 5 to 30 |
| 100° F. | 0 to 15 | more narrowly the following

| Temperatures | Solids (%) |
|---|---|
| 50° F. | at least 30 |
| 70° F. | at least 25 |
| 80° F. | 15 to 30 |
| 92° F. | 10 to 20 |
| 100° F. | 0 to 10 |

The fats of the invention can also be employed in margarines. S.F.I. values required for an oil phase to be used in a stick margarine are a minimum solids content of about 15% at 50° F., a minimum solids content of about 7% at 70° F., and a maximum solids content of about 5% at 92° F. Preferably, the maximim solids content at 92° F. will be less than 4%, most preferably between 1½ to 3½% at 92° F. At this specification, the margarine may be formed and wrapped satisfactorily, maintaining the stick form without substantial oil separation at room temperature and yet remains rapid melting on the tongue at about 98° F. A more preferred SFI profile will show solid contents within the following ranges:

| Temperatures | Solids (%) |
|---|---|
| 50° F. | 16 to 31 |
| 70° F. | 11 to 18 |
| 92° F. | 3.5 maximum |

Desirably, the stick margarine should remain firm at ordinary room temperature up to about 80° F., and will therefore most preferably have an SFI value at this temperature within the range of from about 6 to about 10.

The SFI solids values required for an oil phase to be used in formulating a tub margarine are a minimum solids content of about 8% at 50° F., and a minimum solids content of about 3% at 70° F. and a maximum solids content of about 4% at 92° F. Preferably, the SFI profile shows solids contents in the following ranges:

| Temperatures | Solids (%) |
|---|---|
| 50° F. | 9 to 15 |
| 70° F. | 5 to 10 |
| 92° F. | 3.5 maximum |

An advantage of the invention is that low calorie fats having diverse functional properties may be prepared for different food products by varying the selection of the short, medium and long groups and the proportion of SML/SLM/MSL species. As is illustrated in the Examples that follow, processing conditions such as deodorization and distillation can also effect the properties of the product by enriching it with certain species.

Considerable variation in melting profiles and plastic ranges can be achieved using different triglycerides of this invention. By way of illustration, fats for specific food products have the following example S.F.I.'s:

| Product | Solids (%) at Various Temperatures | | | | |
|---|---|---|---|---|---|
| | 50° | 70° | 80° | 92° | 100° |
| cake | 29 | 19 | 17 | 11 | 7 |
| icing | 28 | 23 | 22 | 18 | 15 |
| cake mix | 40 | 31 | 29 | 21 | 15 |
| frying | 44 | 28 | 22 | 11 | 5 |
| pie crust | 33 | 28 | 22 | 10 | 8 |
| puff pastry | 28 | 25 | 24 | 22 | 19 |

-continued

| Product | Solids (%) at Various Temperatures | | | | |
|---|---|---|---|---|---|
| | 50° | 70° | 80° | 92° | 100° |
| yeast dough | 26 | 20 | 12 | 6 | 3 |

Another advantage of this invention is that the modulation of melting behavior provided by the judicious selection of the kind and relative proportions of the short, medium, and long substituents provides a way of engineering the organoleptic properties of the fats. Greasy or waxy mouthfeels can be eliminated or greatly diminished.

Another advantage of the invention is that since preferred food products formulated with the fats of this invention employ natural oils and fully hydrogenated oils, trans isomers can be reduced or eliminated.

Another advantage of the invention is significant amounts of palmitic acid ordinarily present in oils, shortenings and margarines are replaced with low molecular weight short and medium length acids, and preferred formulations are low in palmitic acid.

Yet another advantage of the invention is that food products prepared using preferred triglycerides of the invention have little unsaturation and are therefore oxidation-resistant. Certain embodiments of the invention are, surprisingly, fully saturated liquid oils. Some fats of this invention are sufficiently stable to be used as frying fats.

EXAMPLES

The following examples are presented to further illustrate and explain the present invention and should not be taken as limiting in any regard. Unless otherwise indicated, all parts and percentages are by weight, and are based on the weight at the particular stage of the processing being described. Solid fat indices (herein abbreviated S.F.I.) are determined using dilatometry according to A.O.C.S. Method Cd 10-57 (1989), reporting solids at 50° F. (10° C.), 70° F. (21.1° C.), 80° F. (26-7° C), 92° F. (33.3° C.), and 100° F. (37.8° C.). Solid fat contents (herein abbreviated S.F.C.) are determined using nuclear magnetic resonance (NMR) according to A.O.C.S. Method Cd 16-81, and are reported for the same temperatures as S.F.I. values unless otherwise indicated. Mettler dropping points (M.D.P.) are determined using a Mettler Thermosystem FP 800 following A.O.C.S. Method Cc 18-80 (1989).

Example 1

This example illustrates the production of fats containing enriched amounts of triglycerides bearing short, medium, and long acid groups.

A mixture of triacetin (4.5 moles, obtained from Aldrich), tributyrin (4.5 moles, obtained from Schweizerhall), medium chain triglycerides (3.0 moles, Neobee TM M-5, obtained from Stepan, containing about 67.9% $C_8$, 31.1% $C_{10}$, and 0.6% $C_{12}$ fatty acid substituents), and fully hydrogenated soybean oil (1 mole, obtained from Vandenberg) is randomly interesterified in the presence of a catalytic amount of sodium methoxide (~0.3%) with vigorous stirring at 100° to 150° C. for 5 to 60 minutes. After cooling the reaction mixture and adding about 5 weight % water, the aqueous phase is removed. The mixture is then bleached using using ≧0.5% bleaching clay (Tonsil Optimum FF) and 1000 ppm citric acid (dissolved in water) is added to decolorize and remove soaps. The treatment is continued ½ to 1 hour at 100° C. under vacuum. The filtrate is vacuum steam deodorized to yield a fat mixture having a M.D.P. of 17.6° C. and an S.F.C. of 42.8% at 32.0° F., 18.1% at 50° F., 0.3% at 70° F., 0.6% at 80° F., and 0% at 92° F. A second batch is deodorized at 260° C.

The samples are characterized by high performance liquid chromatography (HPLC) using two 15×0.46 cm, 5 micron particle size Supelcosil C18 columns (in series) in a Hewlett-Packard Model 1090 instrument coupled to a Varex IIA Evaporative Light Scattering Detector. The data is handled with a Model 79994A Chem Station and expressed as area % values. The results are set out in Table 1 below (ACN=acyl carbon number; RT=retention time).

TABLE 1

Calculated and Observed Effect of Deodorization Temperature on Glycerol Ester Compositions Containing Short, Medium and Long Chain Fatty Acids.

| ACN | MW | RRT | 210° C. Deodorization | | 260° C. Deodorization | |
|---|---|---|---|---|---|---|
| | | | % Calc. | % Found | % Calc. | % Found |
| 22 | 442 | 0.551 | 2.45 | 2.45 | 0.00 | 0.00 |
| 24 | 470 | 0.604 | 27.16 | 25.80 | 2.47 | 2.31 |
| 26 | 498 | 0.688 | 15.35 | 17.00 | 6.93 | 7.00 |
| 28 | 526 | 0.766 | 14.42 | 15.54 | 16.99 | 16.38 |
| 30 | 554 | 0.859 | 17.97 | 27.44 | 32.56 | 39.23 |
| 32 | 582 | 0.942 | 5.76 | 4.20 | 10.44 | 8.98 |
| 34 | 610 | 1.000 | 3.42 | 2.64 | 6.20 | 6.69 |
| 36 | 638 | 1.087 | 2.88 | 1.66 | 5.22 | 4.66 |
| 38 | 666 | 1.243 | 4.42 | 1.21 | 8.01 | 5.82 |
| 40 | 694 | 1.301 | 3.26 | 2.06 | 5.91 | 6.40 |
| 42 | 722 | — | 0.01 | — | 0.02 | — |
| 44 | 750 | 1.403 | 1.79 | — | 3.24 | 2.53 |
| 46 | 778 | 1.463 | 0.73 | — | 1.32 | — |
| | | total | 99.62 | 100.00 | 99.31 | 100.00 |
| | | | $r^2 = 0.9960$ | | $r^2 = 0.9527$ | $r^2 = 0.9909$ |

At 210°, about 3.37% of the total product is made up of SMM structures. This amount is reduced to only 0.2% after deodorization at 260° C. Thus, steam deodorization between 210° and 260° C. stripped off triglycerides containing short, and short and medium chain length acids. These temperatures also are sufficient to volatilize MMM and SSL triesters.

The product recovered from the 260° C. deodorization is further fractionated by feeding it into a Pope ™ 2″ wipe film still configured for molecular distillation. A volatile component (distillate) and a non-volatile component (residue) is obtained. HPLC profiles yield the data set out in Table 2.

TABLE 2

Comparison of Calculated and Observed Compositions of Wiped-Film Distillate and Residue Fractions.

| ACN | MW | RRT | Distillate | | Residue | |
|---|---|---|---|---|---|---|
| | | | % Calc. | % Found | % Calc. | % Found |
| 24 | 470 | 0.618 | 3.20 | 3.93 | | |
| 26 | 498 | 0.688 | 8.99 | 9.61 | | |
| 28 | 526 | 0.759 | 22.03 | 22.93 | | |
| 30 | 554 | 0.857 | 41.98 | 45.95 | 0.56 | 0.47 |
| 32 | 582 | 0.939 | 12.87 | 10.21 | 2.28 | 1.87 |
| 34 | 610 | 1.000 | 5.62 | 5.10 | 8.15 | 5.87 |
| 36 | 638 | 1.083 | 2.72 | 1.82 | 13.70 | 10.24 |
| 38 | 666 | 1.228 | 2.59 | 0.44 | 26.34 | 25.33 |
| 40 | 694 | 1.292 | | | 25.89 | 29.97 |
| 42 | 722 | 1.327 | | | 0.09 | 2.61 |
| 44 | 750 | 1.400 | | | 14.19 | 16.08 |
| 46 | 778 | 1.459 | | | 5.78 | 3.56 |
| 48+ | | | | | 3.02 | — |
| | | total | 100.00 | 99.99 | 100.00 | 96.00 |
| | | | $r^2 = 0.9965$ | $r^2 = 0.9960$ | $r^2 = 0.9740$ | |

TABLE 2-continued

Comparison of Calculated and Observed Compositions of Wiped-Film Distillate and Residue Fractions.

| ACN | MW | RRT | Distillate | | Residue | |
|---|---|---|---|---|---|---|
| | | | % Calc. | % Found | % Calc. | % Found |
| Mass Balance: | | | 77.2 g | 73.1 g | 22.8 g | 26.9 g |

The data shows the effectiveness of the distillation process. The volatile fraction (over 73% of the total product) has been enriched in ACN fractions 24–38 with more than 88.7% occurring between A.C.N. 26–32. The non-volatile fraction, on the other hand, is enriched in A.C.N. fractions 30–46, with 84.1% between fractions 36–44.

Detailed calculations are provided in Table 3.

TABLE 3

Calculated Compositions of Wiped-Film Still Distillate and Residue Fractions.

| ACN | MW | Composition | Type | orig. sample | distillate | residue |
|---|---|---|---|---|---|---|
| 24 | 470 | C4-C10-C10 | SMM | 0.20 | 0.26 | |
| | | C8-C8-C8 | MMM | 0.16 | 0.21 | |
| | | C2-C4-C18 | SSL | 2.00 | 2.59 | |
| | | C4-C4-C16 | SSL | 0.11 | 0.14 | |
| 26 | 498 | C4-C4-C18 | SSL | 5.25 | 6.81 | |
| | | C8-C8-C10 | MMM | 1.14 | 1.48 | |
| | | C2-C8-C16 | SML | 0.54 | 0.70 | |
| 28 | 526 | C8-C10-C10 | MMM | 1.36 | 1.76 | |
| | | C2-C8-C18 | SML | 13.48 | 17.48 | |
| | | C4-C8-C16 | SML | 1.50 | 1.95 | |
| | | C2-C10-C16 | SML | 0.65 | 0.84 | |
| 30 | 554 | C10-C10-C10 | MMM | 0.31 | 0.40 | 0.004 |
| | | C2-C10-C18 | SML | 9.31 | 12.03 | 0.16 |
| | | C4-C8-C18 | SML | 21.85 | 28.22 | 0.38 |
| | | C4-C10-C16 | SML | 1.03 | 1.33 | 0.018 |
| 32 | 582 | C4-C10-C18 | SML | 9.84 | 12.13 | 2.15 |
| | | C8-C8-C16 | MML | 0.60 | 0.74 | 0.13 |
| 34 | 610 | C8-C8-C18 | MML | 5.60 | 5.08 | 7.36 |
| | | C8-C10-C16 | MML | 0.53 | 0.48 | 0.70 |
| | | C2-C16-C16 | SLL | 0.07 | 0.06 | 0.09 |
| 36 | 638 | C8-C10-C18 | MML | 5.04 | 2.62 | 13.23 |
| | | C10-C10-C16 | MML | 0.11 | 0.06 | 0.29 |
| | | C4-C16-C16 | SLL | 0.07 | 0.04 | 0.18 |
| 38 | 666 | C10-C10-C18 | MML | 1.12 | 0.36 | 3.68 |
| | | C2-C18-C18 | SLL | 5.64 | 1.83 | 18.53 |
| | | C4-C16-C18 | SLL | 1.25 | 0.40 | 4.12 |
| 40 | 694 | C4-C18-C18 | SLL | 5.87 | | 25.71 |
| | | C8-C16-C16 | MLL | 0.04 | | 0.18 |
| 42 | 722 | C10-C16-C16 | MLL | 0.02 | | 0.09 |
| 44 | 750 | C8-C18-C18 | MLL | 2.95 | | 12.92 |
| | | C10-C16-C18 | MLL | 0.29 | | 1.27 |
| 46 | 778 | C10-C18-C18 | MLL | 1.32 | | 5.78 |
| 48 | 806 | C16-C16-C16 | LLL | 0.0007 | | 0.003 |
| 50 | 834 | C16-C16-C18 | LLL | 0.02 | | 0.09 |
| 52 | 862 | C16-C18-C18 | LLL | 0.16 | | 0.70 |
| 54 | 890 | C18-C18-C18 | LLL | 0.51 | | 2.23 |
| | | totals: | | 99.9407 | 100.00 | 99.995 |

The SML structures that have been concentrated in the distillate fraction are predicted to have a high degree of structural diversity, and this is reflected in Table 4 data.

TABLE 4

Mass Spectroscopic Confirmation of Molecular Weight Assignments Made by Correlation of HPLC Rentention Times with Acyl Carbon Number Ranking.

| Retention Time, R.T. (minutes) | Relative R.T. | Acyl Carbon Number (A.C.N.) | Molecular Weight | |
|---|---|---|---|---|
| | | | Calculated | Observed |
| 10.2–10.7 | 0.620 | 24 | 470 | 470 |
| 11.4–11.9 | 0.691 | 26 | 498 | 498 |
| 12.8–13.5 | 0.780 | 28 | 526 | 526, 526 |
| 14.6–15.1 | 0.881 | 30 | 554 | 554, 554 |

TABLE 4-continued

Mass Spectroscopic Confirmation of Molecular Weight
Assignments Made by Correlation of HPLC
Rentention Times with Acyl Carbon Number Ranking.

| Retention Time, R.T. (minutes) | Relative R.T. | Acyl Carbon Number (A.C.N.) | Molecular Weight Calculated | Molecular Weight Observed |
|---|---|---|---|---|
| 16.2–16.3 | 0.964 | 32 | 582 | 582 |
| 16.4–17.3 | 1.000 | 34 | 610 | 610 |
| 17.4–18.8 | 1.074 | 36 | 638 | 638 |
| 20.3–21.5 | 1.240 | 38 | 666 | N.D. |

Table 4 predicts eight unique combinations of S, M and L acids. Each of these would be expected to exist as a 1:1:1 ratio of the three isomeric SML forms. This brings the number of possible SML-type structures (including isomers) to a total of 24. These are all contained within the envelope defined by A.C.N. fractions 26 to 32. Since the actual HPLC data correlates well in magnitude to the sum of these respective four A.C.N. fractions, a detailed description of the structural information contained within the aggregate HPLC peaks is made possible through the viewing perspective provided by the calculations.

The juxtaposition of calculation versus observation is verified by the assignment of A.C.N. values to HPLC peaks by mass spectrometry. The distillate fraction is examined by tandem chemical ionization mass spectrometry, and the results shown in Table 4 support the theoretical assignments precisely. In this mass spectral examination, the HPLC peaks associated with molecular masses 526 and 554 actually are resolved into two peaks each, giving rise to two discernible compounds having mass 526 and two having mass 554.

For a second verification approach, the SML-rich distillate is examined by quantitative carbon-13 NMR in $C_6D_6$ solution using a Varian VXR400 spectrometer. The relative molar acid compositions are determined by integration of the respective carbon chemical shifts: 35.8–36.2 ppm ($CH_2$ alpha to $C=O$ of butyric acid), 34.0–34.3 ppm ($CH_2$ alpha to $C=O$ of medium and long acid chains), 32.0–32.4 ppm ($CH_2$ beta to terminal methyl of medium and long acid chains), 29.2–30.4 ppm (all non-assigned carbons in medium and long chain acids), 25.2 ppm ($CH_2$ beta to $C=O$ in medium and long acid chains), 23.0–23.2 ppm ($CH_2$ alpha to terminal methyl of medium and long acid chains), 20.2–20.5 ppm ($CH_3$ of acetic acid), 18.6 ppm ($CH_2$ alpha to terminal methyl of butyric acid), 14.2–14.4 ($CH_3$ of medium and long chain acids) and 13.6 ($CH_3$ of butyric acid). The results are summarized in Table 5, compared with values calculated from the information contained in Table 3. It can be seen there is good agreement between the theoretical and experimental data so that the reaction can be modelled to develop a prediction of the products.

TABLE 5

Comparison of Calculated Short, Medium and Long Chain Acid Composition with Results Obtained by Quantitative Carbon-13 NMR.

| | Mole % | | | |
|---|---|---|---|---|
| | Acetic | Butyric | Medium Chain | Long Chain |
| Calculated | 12.14 | 20.62 | 34.74 | 32.50 |
| Found | 13.9 | 20.2 | 26.7 | .2 |

In summary, the original sample deodorized at 260° C. contained an estimated 57.3% of SML structures distributed over A.C.N. fractions 26 to 32. In the distillate there is an enrichment of these SML triester types to an estimated level of 74.7%. The residue, on the other hand, is dominated by the higher molecular weight MML and SLL triesters (25.5% and 48.7% respectively), and contains only about 2.8% residual structures. Not only has the SML fraction been enriched, but the technique facilitates the ready monitoring of what is happening to novel SML compositions during molecular distillation.

Example 2

This example illustrates the preparation of other triglyceride mixtures bearing short, medium, and long substituents. It also shows, by providing a comparison of these triglycerides with those bearing short and long substituents, how adding medium chain triglycerides to an interesterifiction mixture of short and long triglycerides can drastically alter the melting profiles of the fat produced in the reaction. Moreover, steam deodorization at 260° C. enriches the product with desirable SML/SLM/MSL species.

Fat mixtures are prepared by interesterifying hydrogenated canola (refined, low erucic rapeseed oil containing ≦4% palmitic acid, hydrogenated at 180° C. and 60 lbs hydrogen until the Iodine Value (IV) is ≦3) with short or short and medium triglycerides (set out below).

One molar equivalent hydrogenated canola (899 g) and the molar equivalents of short and/or medium triglycerides set out below are interesterified in the presence of 0.2 to 0.3% sodium methoxide by heating to ~110° C. with agitation under a vacuum for about half an hour until color develops. (The M.D.P. may be checked at this time, and the reaction continued if the M.D.P. has not dropped sufficiently.) Phosphoric acid (~0.2 to ~0.5%, at least twice the amount of sodium methoxide) is added to stop each reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The treatment is continued for ½ to 1 hour at 110° C. The products are cooled to 80° C., filtered, and steam deodorized at 210° C. for 2 to 3 hours.

Using this procedure, a steam deodorized product obtained by interesterifying triacetin and tripropionin with hydrogenated canola yields the following mixtures:

| | | Hydrogenated Canola:Triacetin:Tripropionin Reactant Molar Ratio | | | | | |
|---|---|---|---|---|---|---|---|
| | | 1:11:1 | 1:3:9 | 1:6:6 | 1:9:3 | 1:2:10 | 1:1:11 |
| M.D.P., | °C. | 33.8° | 26.7° | 29.8° | 32.2° | 27.6° | 27.7° |
| S.F.I. | 50° F. | | 49.2 | 61.2 | 65.8 | 57.2 | 60.9 |
| | 70° F. | 65.4 | 25.2 | 49.8 | 61.7 | 37.5 | 40.1 |
| | 80° F. | 58.8 | 4.0 | 32.4 | 50.0 | 8.2 | 5.9 |
| | 92° F. | 14.9 | 0 | 0 | 0.3 | 0 | 0 |
| | 100° F. | 0.2 | 0 | 0 | 0 | 0 | 0 |

Substituting medium chain triglycerides (obtained from Stepan Chemicals) for tripropionin the interesterification mixture yields a pronounced change in melting characteristics of the product. Steam deodorized products obtained by interesterifying 1 mole hydrogenated canola, 6 moles triacetin and 6 moles medium chain triglycerides yields a fat having a M.D.P. of 21° C., and a S.F.I. of 1.5% at 50° F. and 0% at 70° F.

and above. Similarly, interesterification of 1 mole hydrogenated canola, 3.48 moles triacetin and 9 moles medium chain triglycerides yields a liquid oil having a M.D.P. of 20.3° C. and no solids at 50° to 100° F.

Similar results are achieved when hydrogenated soybean oil is employed in the same procedure in place of hydrogenated canola. When 11 moles triacetin and 1 mole tripropionin are interesterified with 1 mole hydrogenated soybean oil, the steam deodorized product has a M.D.P. of about 35° C., and an S.F.C. of 88.6% at 50° F., 86.3% at 70° F., 81.1% at 80° F., 10.4% at 92° F., and 0% at 100° F. When 9 moles triacetin and 3 moles medium chain triglycerides are interesterified with 1 mole of the same hydrogenated soybean oil, the melting profile is lowered considerably. The steam deodorized product has a M.D.P. of 22.6° C., and an S.F.C. of 50.5% at 32° F., 30.4% at 50° F., 3.9% at 70° F., 0.2% at 80° F., and 0% at 92° F.

Employing butyric acid residues as the short chain component further lowers the melting curve. Thus, as set out in the last Example, random interesterification of 4.5 moles triacetin, 4.5 moles tributyrin, and 3.0 moles medium chain triglycerides with 1.0 moles hydrogenated soybean oil under the same conditions yields a fat mixture having a M.D.P. of 17.6° C. and an S.F.C. of 42.8% at 32.0° F., 18.1% at 50° F., 0.3% at 70° F., 0.6% at 80° F., and 0% at 92° F. Similarly, random interesterification of 9.6 moles tributyrin and 2.4 moles medium chain triglycerides with 1 mole hydrogenated soybean oil yields a triglyceride mixture having a M.D.P. of 14.5° C. and an S.F.C. of 36.0% at 32° F., 12.0% at 50° F., 0.2% at 70° F., and 0% at 80° F. Again, employing medium chain triglycerides in the reaction mixture further lowers the melting profile of the product; a glyceride mixture prepared by the random interesterification of 9 moles tributyrin and 3 moles medium chain triglycerides with 1 mole hydrogenated soybean oil followed by steam deodorization has a M.D.P. of 12.9° C., and an S.F.C. of 23.9% at 32° F., 4.4% at 50° F., and 0% at 70° F. Interesterification of 8.0 moles tributyrin and 4 moles medium chain triglycerides with 1 mole hydrogenated soybean oil followed by steam deodorization yields a fat mixture having an M.D.P. of 6.9° C. and an S.F.C. of 12.6% at 32° F., 0.4% at 50° F., 0.2% at 70° F., and 0% at 80° F.

Additional desirable mixtures can be achieved by increasing the temperature of the steam deodorization. Random interesterification of 10 moles triacetin and 2.0 moles medium chain triglycerides with 1 mole hydrogenated canola followed by steam deodorization at 260° C. rather than 210° C. for about 2 hours yields a fat mixture having a M.D.P. of 31.8° C° C. and an S.F.C. of 77.8% at 32° F., 70.8% at 50° F., 45.1% at 70° F., 24.7% at 80° F., 1.1% at 92° F., and 1.8% at 100° F.

Example 3

This example further illustrates that the melting characteristics of triglycerides bearing short, medium and long residues can be modulated significantly by changing the relative proportions of short and medium substituents in the reaction mixture, and by increasing the steam deodorization temperature.

Using the preparation and purification procedures of Example 2, hydrogenated canola (H-Canola) is interesterified with short and/or medium triglycerides to obtain the following mixtures:

|  |  | Hydrogenated Canola:Triacetin:Tripropionin Reactant Molar Ratio | | | |
|---|---|---|---|---|---|
|  |  | 1:4:0.5 | 1:3.5:1 | 1:3:1.5 | 1:2.5:2 |
| M.D.P., | °C. | 35.4° | 35.1° | 33.9° | 34.1° |
| S.F.I. | 50° F. | 70.0% | 69.4% | 68.5% | 69.8% |
|  | 70° F. | 67.8% | 66.6% | 65.4% | 65.0% |
|  | 80° F. | 62.6% | 59.6% | 56.8% | 53.5% |
|  | 92° F. | 25.6% | 17.0% | 8.7% | 4.1% |
|  | 100° F. | 0 | 0 | 0 | 0 |

Incorporation of medium chain triglycerides for a portion of the short triglycerides in the interesterification reaction followed by steam deodorization yields the following mixtures:

|  |  | H-Canola:Triacetin: Tripropionin:MCT Reactant Molar Ratio | |
|---|---|---|---|
|  |  | 1:3.84:1.25:0.25 | 1:0.94:3.16:0.33 |
| M.D.P., | °C. | 23.5° | 31.5 |
| S.F.I. | 50° F. | 60.5 | 59.3 |
|  | 70° F. | 44.2 | 43.0 |
|  | 80° F. | 22.5 | 25.9 |
|  | 92° F. | 0 | 0 |
|  | 100° F. | 0 | 0 |

Note that in contrast to Example 2, which described interesterifications comprising reactant molar ratios of about 12 short and/or medium residues to 1 mole of long chain residues, the ratio here is about 4 or 5 to 1. In addition, the substitution of 5 to 8% of the short chain reactants with medium chain reactants results in a solids content at 50° F. only slightly lower than mixtures containing all short and long substituents. At 70° F., however, the substitution results in about 30% less solids; at 80° F., the substitution results in about 60% less solids; and at 100° F., the substitution results in 100% less solids. It can be seen that the resulting overall melting profiles are less sharp and the fats more plastic with the use of medium residues with short.

Random interesterification of 6.0 moles tributyrin and 2.0 moles medium chain triglycerides with 1 mole hydrogenated soybean oil followed by steam deodorization as described in Example 2 yields a fat mixture having a M.D.P. of 17.1° C. and an S.F.C. of 49.6% at 32° F., 23.5% at 50° F., 0.6% at 70° F., 0.7% at 80° F., 0.6% at 92° F., 0.3% at 100° F., and 0.4% at 104° F. Using the same procedure, interesterification and steam deodorization of 7.5 moles tributyrin and 2.5 moles medium chain triglycerides with 1 mole hydrogenated soybean oil followed by steam deodorization as described in Example 2 yields a fat mixture having a M.D.P. of 15.7° C. and an S.F.C. of 39.9% at 32° F., 14.6% at 50° F., 0.2% at 70° F., 0.1% at 80° F., 0.3% at 92° F., and 0.5% at 100° F. Thus, use of butyric acid residues in combination with medium and long can result in further lowering of the melting profile.

Additional desirable mixtures can be achieved by varying processing conditions. Random interesterification of 3 moles triacetin and 1.0 mole medium chain triglycerides with 1 mole hydrogenated soybean oil followed by steam deodorization at 260° C. for 2 hours yields a fat mixture having a M.D.P. of 35.2° C. and an S.F.C. of 86.7% at 32° F., 81.5% at 50° F., 66.5% at 70° F., 44.0% at 80° F., 8.0% at 92° F., 0.6% at 100° F., and 0.0% at 104° F.

These effects are further illustrated by way of the random interesterification of 6 moles triacetin and 1 mole medium chain triglycerides with 1 mole hydrogenated high erucic rapeseed oil (sample A), 6 moles triacetin and 2 moles medium chain triglycerides with 1 mole hydrogenated high erucic rapeseed oil (sample B), and 6 moles tributyrin and 2 moles medium chain triglycerides with 1 mole hydrogenated high erucic rapeseed oil (sample C), followed by steam deodorization at 260° C. for 2 hours, yielding mixtures having the following physical properties:

|  |  | (A) | (B) | (C) |
|---|---|---|---|---|
| M.D.P., | °C | 45.1° | 42.1° | 35.1° |
| S.F.C. | 32° F. | 88.5% | 82.5% | 74.9% |
|  | 50° F. | 86.4% | 79.9% | 69.1% |
|  | 70° F. | 82.1% | 73.1% | 49.5% |
|  | 80° F. | 77.4% | 64.8% | 31.1% |
|  | 92° F. | 59.2% | 38.2% | 1.9% |
|  | 100° F. | 43.2% | 17.6% | 0.1% |
|  | 104° F. | 28.2% | 4.3% | — |

Example 4

This Example illustrates that further modulation of the melting properties can be achieved by varying the long residues as well as by mixing medium with short and medium substituents and by varying processing conditions.

Interesterifications and steam deodorizations are carried out as described in Example 2 above, except that high erucic rapeseed obtained from CSP, hydrogenated to an IV≦3 (hereafter denoted H-HEAR), is added to the reaction mixture with hydrogenated canola (H-Canola).

Using only short chain triglycerides, the following triglyceride mixtures are obtained:

|  |  | H-Canola:H-HEAR:Triacetin:Tripropionin Reactant Molar Ratio | | | | |
|---|---|---|---|---|---|---|
|  |  | 0.9:0.1: 11:1 (D) | 0.9:0.1:5:3 (E) | 0.9:0.1: 6:6 (F) | 0.9:0.1: 1:11 (G) | 0.9:0.1:3:9 (H) |
| M.D.P., | °C. | 35.4° | 33.0° | 30.4° | 31.0° | 30.8° |
| S.F.I. | 50° F. | 70.2 | 68.7 | 58.9 | 64.6 | 60.5 |
|  | 70° F. | 68.4 | 64.1 | 46.9 | 53.1 | 47.3 |
|  | 80° F. | 63.8 | 52.3 | 28.4 | 26.2 | 23.4 |
|  | 92° F. | 33.1 | 7.2 | 0.3 | 0 | 0 |
|  | 100° F. | 0.2 | 0 | 0.2 | 0 | 0 |

Substituting medium chain triglycerides for the tripropionin in the interesterification mixture results in the following triglyceride mixtures:

|  |  | H-Canola:H-HEAR:Triacetin:MCT Reactant Molar Ratio | | |
|---|---|---|---|---|
|  |  | 0.9:0.1:5.7:0.3 (I) | 0.9:0.1:8.6:3.4 (J) | 0.9:0.1:5.7:6.3 (K) |
| M.D.P., | °C. | 34.3° | 24.5° | 11.1° |
| S.F.I. | 50° F. | 63.5 | 30.9 | 1.3 |
|  | 70° F. | 56.3 | 6.5 | 0 |
|  | 80° F. | 46.3 | 0 | 0 |
|  | 92° F. | 16.2 | 0 | 0 |
|  | 100° F. | 0.4 | 0 | 0 |

It can be seen from a comparison of mixtures E and F that, with this array of long substituents and a reactant molar ratio of short to long substituents of about 6 or 8 to 1, substitution of 5% of the acetic acid residues with medium chain residues results in a mixture (I) having similar properties to one having 37% of the acetic acid residues replaced with propionic (E), except that the overall melting profile is less steep.

However, comparing D, F, G, and H with J and K shows that with a reactant molar ratio of about 12 to 1 and the same array of long substituents, a substitution of 28 to 52% of the short substituents with medium chain moieties has a drastic effect on the melting properties. At 50° F., the solids content drops 50% to 98%, at 70° F., the drop is 88% to 100%, and at 80° F., it is 100%. This more pronounced modulation of melting profiles at higher medium chain levels is analogous to the results reported in Example 2.

The modulation can be further varied by varying processing conditions to yield fat mixtures enriched with SML species. Steam deodorizing sample K at 260° C. rather than 210° C. yields a product that had an M.D.P. of 19.6° C. and 19.8% solids at 50° F., with no solids at 70° to 100° F. Likewise, randomly interesterifying 4.5 moles triacetin, 4.5 moles tributyrin and 3.0 moles medium chain triglycerides with 1.0 mole hydrogenated soybean oil using the procedure of Example 2 followed by steam deodorization at 260° C. for 2 hours yields a mixture having a M.D.P. of 22.2° C., and an S.F.C of 70.5% at 32° F., 52.6% at 50° F., 4.8% at 70° F., 0.2% at 80° F., and 0% at 92° F.

Example 5

This Example further illustrates variations in melting characteristics of short/long triglycerides that can be achieved by using medium chain moieties at different levels, by varying the proportion of short and/medium to long, by varying the long substituents, and by varying processing conditions.

Interesterification and steam deodorizations are carried out as described in Example 4 above, except that liquid canola (L-Canola) is added to the reaction mixture. Using short chain triglycerides, the following mixtures are obtained:

|  |  | H-Canola:L-Canola:H-HEAR:Triacetin: Tripropionin Reactant Molar Ratio | | |
|---|---|---|---|---|
|  |  | 0.8:0.1:0.1:3:9 (L) | 0.8:0.1:0.1:9:3 (M) | 0.8:0.1:0.1:6:6 (N) |
| M.D.P., | °C. | 32.2° | 30.8° | 30.2° |
| S.F.I. | 50° F. | 55.7 | 55.8 | 50.8 |
|  | 70° F. | 42.8 | 44.8 | 34.6 |
|  | 80° F. | 32.4 | 31.7 | 18.4 |
|  | 92° F. | 0 | 0 | 0 |
|  | 100° F. | 0 | 0 | 0 |

Substituting medium chain triglycerides for tripropionin in the reaction yields the following mixtures:

|  |  | H-Canola:L-Canola:H-HEAR:Triacetin:MCT Reactant Molar Ratio | | | |
|---|---|---|---|---|---|
|  |  | 0.7:0.2: 0.1:5.7:0.3 (O) | 0.76:0.2: 0.04:2.5: 0.3 (P) | 0.64:0.27: 0.09:5.2:0.3 (Q) | 0.7:0.2: 0.1:5.7:6.3 (R) |
| M.D.P., | °C | 30.9° | 27.7° | 29.1° | 8.2° |
| S.F.I. | 50° F. | 40.6 | 41.4 | 34.4 | 0 |
|  | 70° F. | 28.9 | 25.6 | 21.8 | 0 |
|  | 80° F. | 15.2 | 13.8 | 8 | 0 |
|  | 92° F. | 0 | 0 | 0 | 0 |
|  | 100° F. | 0 | 0 | 0 | 0 |

As in previous examples, comparing L, M, and N, with R shows that, with similar short to long reactant ratios and similar arrays of long substituents, substitution of 52% of the short residues with medium residues results in a large solids profile drop: 100% at 50° to 80° F. Processing conditions vary the effects. Deodorized at 260°, sample R has an M.D.P. of 15.1° C., 4.6% solids at 50° F. and no solids at 70° to 100° F.

Where fewer medium moieties are introduced, the effect is less pronounced (mixtures O, P and Q), yet more plasticity is achieved.

This finding is confirmed in another series of experiments. Triglycerides bearing short and medium residues and long residues derived from a mixture of hydrogenated canola, liquid canola, and hydrogenated cottonseed oil (H-CS) are prepared using the interesterification and steam deodorization procedure outlined in Example 2 to yield the following mixtures:

| | | H-Canola:L-Canola:H-CS:Triacetin: Tripropionin:MCT Reactant Molar Ratio | | |
|---|---|---|---|---|
| | | 0.44:0.22:0.33: 4.4:0:0.33 | 0.43:0.22:0.35: 0:4.35:0.32 | 0.38:0.32:0.3: 2.16:2.16:0.32 |
| M.D.P., | °C. | 27.2° | 23.5° | 23.2° |
| S.F.I. | 50° F. | 28.7 | 28.6 | 23.2 |
| | 70° F. | 12.2 | 4.1 | 4.3 |
| | 80° F. | 0 | 0 | 0 |
| | 92° F. | 0 | 0 | 0 |
| | 100° F. | 0 | 0 | 0 |

Example 6

In this example, other desirable fat mixtures of this invention are prepared by interesterifying long chain triglycerides comprising a hydrogenated oil or a hydrogenated oil mixture, with short chain triglycerides comprising tripropionin and/or triacetin, and medium chain triglycerides. An unhydrogenated (liquid) oil is, optionally, included.

Using the procedure of Example 2, the following reactants are interesterified:

| Reactant | S | T | V |
|---|---|---|---|
| | | Moles Reactant | |
| Hydrogenated Canola | 0.8 | 0.9 | 0.76 |
| Liquid Canola | 0 | 0 | 0.2 |
| Hydrogenated Rapeseed | 0 | 0.1 | 0.04 |
| Medium Triglycerides | 0.2 | 0.3 | 0.3 |
| Tripropionin | 3.0 | 2.85 | 0 |
| Triacetin | 1.0 | 0.85 | 3.0 |

The initial M.D.P. of reaction mixture T is 61.4° C. and the final is 26.6° C. The final M.D.P. of mixture S is 15.9° C. and of mixture U is 30.5° C. The purified products (steam deodorized at 210° C.) have the following physical properties:

| | | V | W | X |
|---|---|---|---|---|
| M.D.P., | °C | 22.5 | 31.5 | 30.5 |
| S.F.I. | 50° F. | 60.5 | 59.3 | 41.4 |
| | 70° F. | 44.2 | 43.0 | 25.6 |
| | 80° F. | 22.5 | 25.9 | 13.8 |
| | 92° F. | 0 | 0 | 0 |

As illustrated in the above examples, employing butyric acid residues further lowers the melting profile. The random interesterification of 9 moles tributyrin and 3 moles medium chain triglycerides with 0.8 mole hydrogenated soybean oil and 0.2 moles liquid soybean oil followed by steam deodorization as set out in Example 2 yields an oil having an M.D.P. of 5.8° C. and an S.F.C. of 10.4% at 32° F., 0.1% at 50° F., 0.2% at 70° F., and 0% at 80° F. Using the same procedure and more liquid oil, the effect is more pronounced: interesterification of 9 moles tributyrin and 3 moles medium chain triglycerides with 0.6 mole hydrogenated soybean oil and 0.4 moles liquid soybean oil yields an oil having an M.D.P. of 1.3° C. and an S.F.C. of 6.7% at 32° F., 0% at 50° F., 0.3% at 70° F., and 0% at 80° F.

Example 7

This example illustrates the preparation of a stick margarine spreadable at refrigerator temperature which has as the fat phase, short/medium/long plastic fats of this invention.

Short/medium/long triglycerides are first prepared. A random interesterification between 5.7 moles triacetin, 6.3 moles medium chain triglycerides, 0.9 moles hydrogenated canola, and 0.1 mole hydrogenated high erucic rapeseed oil is carried out as described in Example 2, and the product is steam deodorized at 215° C. for 2 hours, yielding a fat having a M.D.P. of 19.6° C. NMR fatty acid analysis shows the mixture contains about 18 mole % short, 56 mole % medium, and 25 mole % long moieties.

This is employed as the fat in a stick margarine prepared by emulsifying

| | parts |
|---|---|
| Oil Phase Ingredients | |
| SML Fat | 80 |
| Lecithin | 0.17 |
| Soybean Oil (<5 IV) | 0.21 |
| Mono- and Diglycerides | |
| Margarine Flavor and Color | 0.0062 |
| with Aqueous Phase Ingredients | |
| Water | 16.4 |
| Whey | 1.00 |
| Salt | 2.00 |
| Sodium Benzoate | 0.086 | and passing the emulsion through a cooled, scraped-surface heat exchanger in the usual process.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are meant to cover the claimed components and stps in any sequence which is effective to meet the objectives there intended, unless the context specifically indicates the contrary.

We claim:

1. A food composition having a fat ingredient wherein at least 24% of the fat ingredient comprises triglycerides selected from the group consisting of

and mixtures of these,
where
- each L group is, independently, a long chain saturated aliphatic group having 15 to 21 carbons;
- each M group is, independently, a medium chain saturated aliphatic group having 5 to 11 carbons; and
- each S, independently, is a short chain group having 1 to 3 carbons.

2. A composition according to claim 1 wherein at least about 34% of the fat ingredient comprises a mixture of SML, SLM, and MSL triglycerides.

3. A composition according to claim 2 wherein at least about 50% of the fat ingredient comprises a mixture of SML, SLM, and MSL triglycerides.

4. A composition according to claim 1 wherein at least about 70% of the L groups are derived from an acid selected from the group consisting of stearic acid, behenic acid, and mixtures of these; at least about 90% of the M groups are derived from an acid selected from the group consisting of capric acid, caprylic acid and mixtures of these; and the S groups are derived from an acid selected from the group consisting of acetic acid, butyric acid, and mixtures of these with each other and with propionic acid.

5. A composition according to claim 4 wherein the L groups are a mixture of groups derived from a hydrogenated oil selected from the group consisting of hydrogenated soybean oil, hydrogenated canola, hydrogenated high erucic rapeseed, and mixtures thereof.

6. A composition according to claim 4 wherein the triglycerides have an acyl carbon number of 28 to 32.

7. A composition according to claim 4 wherein the triglycerides have an acyl carbon number of 32 to 36.

8. A composition according to claim 1 wherein the triglycerides are liquid at room temperature.

9. A composition according to claim 1 wherein the triglycerides are spreadable at refrigerator temperatures.

10. A low calorie fat composition wherein at least about 30% of the composition comprises triglyceride molecules each bearing short $C_2$ to $C_4$ short acid residues, medium $C_8$ to $C_{12}$ saturated acid residues, and long, saturated $C_{16}$ to $C_{22}$ fatty acid residues having an acyl carbon number of 26 to 36.

11. A composition according to claim 10 wherein at least about 50% of the composition comprises the triglycerides.

12. A composition according to claim 10 wherein at least about 85% of the long residues are derived from stearic acid and at least about 90% of the medium residues are derived from capric acid, caprylic acid or a mixture of capric and caprylic acid.

13. A composition according to claim 12 wherein the short acid residues are derived from a mixture of acetic and propionic acid or a mixture of acetic and butyric acid.

14. A composition according to claim 13 wherein the triglycerides contain about 14 mole % acetic acid residues, about 20 mole % butyric acid residues, about 27 mole % medium chain residues and about 39 mole % long chain residues.

* * * * *